United States Patent [19]
Stoilov et al.

[11] Patent Number: 5,935,605
[45] Date of Patent: *Aug. 10, 1999

[54] ORAL PREPARATION FOR PATIENTS WITH CHRONIC RENAL INSUFFICIENCY, METHOD OF MAKING AND USE

[76] Inventors: Ivan Lubomirov Stoilov, 2262 E. Rule Ave., Maryland Heights, Mo. 63043; Tzvetan Dimitrov Georgiev, 57 Georgi Kirkov bulevard, Sofia, Bulgaria; Mille Vasilev Taskov, 30 Vladimir Zaimov bulevard, Sofia, Bulgaria; Iskra Dimitrova Koleva, j.k. "Mladost", Sofia, Bulgaria

[ * ] Notice: This patent issued on a continued prosecution application filed under 37 CFR 1.53(d), and is subject to the twenty year patent term provisions of 35 U.S.C. 154(a)(2).

[21] Appl. No.: 08/812,446

[22] Filed: Mar. 6, 1997

Related U.S. Application Data

[63] Continuation of application No. 08/230,966, Apr. 21, 1994, abandoned.

[51] Int. Cl.⁶ .............................. A61K 35/24; A23J 1/00; A01N 37/18
[52] U.S. Cl. ................................ 424/537; 426/656; 514/2
[58] Field of Search ........................... 424/537; 426/656; 514/2

[56] References Cited

U.S. PATENT DOCUMENTS

| | | | |
|---|---|---|---|
| 3,857,966 | 12/1974 | Feldman et al. | 426/7 |
| 4,075,195 | 2/1978 | Roland | 260/119 |
| 4,443,540 | 4/1984 | Chervan et al. | 435/69 |
| 4,465,696 | 8/1984 | Strahl | 426/63 |
| 4,499,076 | 2/1985 | Ohashi et al. | 424/143 |
| 4,529,612 | 7/1985 | Robson | 426/658 |
| 4,665,158 | 5/1987 | Armanet et al. | 530/357 |
| 4,990,344 | 2/1991 | Euber et al. | 426/28 |
| 5,002,076 | 3/1991 | Altobelli et al. | 132/206 |
| 5,728,678 | 3/1998 | Trimbo et al. | 514/12 |

OTHER PUBLICATIONS

Sautier et al., "The nutritive value of Spirulina algae", Annales Nutrition Alimentation 29 (6):517–534 (1975).
Blakiston's Gould Medical Dictionary p. 626, 1984.
Blakiston's Gould Medical Dictonary Fourth Edition p. 626, 1984.

*Primary Examiner*—Sandra E. Saucier
*Attorney, Agent, or Firm*—Polster, Lieder Woodruff & Lucchesi, LC

[57] ABSTRACT

An oral preparation for use in patients with chronic renal insufficiency or other protein metabolic disorders and method of preparing the protein hydrolysate used therein. The oral preparation has a water soluble enzymatic protein hydrolysate rich in essential amino acids and low in salt content derived from a natural source such as algae, blue-green algae or fish. The water soluble protein hydrolysate is combined with a high calorie source such as natural bee honey. Approximately 5% to 30% of the protein hydrolysate is combined with 70% to 95% of natural bee honey to provide an optimum calorie to protein ratio. The oral preparation is administered in doses of 30 grams to 150 grams per day in one to four divided doses. The preparation maybe administered orally or through a nasogastric feeding tube.

9 Claims, 2 Drawing Sheets

ORAL PREPARATION FOR PATIENTS WITH CHRONIC RENAL INSUFFICIENCY, METHOD OF MAKING AND USE

This is a continuation of Ser. No. 08/230,966 filed Apr. 21, 1994, now abandoned.

BACKGROUND OF THE INVENTION

This invention relates generally to an oral preparation to be used in the prevention and treatment of chronic renal insufficiencies as well as other diseases related to protein metabolism disorders, more specifically to an oral product containing a protein hydrolysate rich in essential amino acids, optimum carbohydrate to protein ratio, and reduced salts, phosphates, and heavy metal content.

It is known that a person with chronic renal insufficiency, kidney disease or damage, or other similar disorders suffer from the effects of the build up of toxic chemicals in the blood, such as ammonia, increased levels of urea, creatinine and other toxic products and metabolites. The level of the concentration of the toxic products varies according to the degree of renal failure. Patient's suffering from chronic renal insufficiency may also suffer from disorders of protein synthesis, anemia, hemopoeisis, hyperlipoproteinemia, disorders of the acid—alkaline and ionic balance and other metabolic disorders.

Generally, the treatment of end stage forms of chronic renal insufficiency is hemodialysis, which is expensive, has side effects, including both physical side effects as well as psycological side effects. In some cases, due to presence of cardiac problems or cardiac decompensation, anemia, or other blood disorders, hemodialysis is inappropriate. All patients suffering from renal disorders, including those who are not good candidates for hemodialysis, would greatly benefit from prophylaxis and treatment with oral therapy to relieve or reverse the symptoms of chronic renal insufficiency, including hyperazotemia and other metabolic disorders.

In the traditional prophylactic oral treatment of nitrogen retention and hyperazotemia in patients with chronic renal insufficiency special attention is usually paid to diet and nutritional therapy. One goal is to reduce the overall oral intake of nitrogen containing compounds such as proteins and toxic non-protein nitrogen containing compounds. Another goal of diet therapy in patients with chronic renal insufficiency was to stimulate the metabolic turnover process in which the ammonia by-products in the blood are reused in the creation of amino acids, purines and other biologically important nitrogen containing compounds so as to reduce the circulating levels of ammonia. Other objects of nutritional therapy are to normalize the electrolyte values, reduce hyperlipidemia, correct hyperphosphatemia, and to reduce the filtration load on the kidneys.

The disadvantages of the known oral therapies for the prophylaxis and treatment of chronic renal insufficiency and hyperazotemia are well known. For example, oral essential amino acids supplements and foods such Amin-Aid (American McGaw), and Travasorb Renal Powder (Travenol Laboratories) are expensive, and have high osmolalities. Treatment can result in osmotic diarrhea, which can exacerbate electrolyte problems.

Essential amino acid products are also provided for intravenous infusion, for example Nephramine (American McGaw) or Renamin (Travenol Laboratories). These products, however, are also very expensive and require intravenous administration. The essential amino acids products are mixed with high density dextrose solution to obtain an appropriate calorie to nitrogen ratio. The solutions are generally introduced through a central venous catheter. The risks associated with central venous administration of amino acid solutions, such as emboli, infection, fluid overload, etc., are well documented.

Recently, oral forms of deaminated aminoacids (alpha-ketoacids), such as ketosteril (Fresenius, Republic of Germany), have been used for controlling circulating ammonia in patients with renal failure. The alpha-ketoacids function by utilizating circulating nitrogen to create proteins. However alpha-ketoacid products are very expensive, not readily accessible, and do not provide a ready source of energy.

Besides treating patients suffering from chronic renal insufficiency with essential amino acids or alpha-ketoacids, other traditional therapy is used. For example, some patients are treated with diuretics to increase the excretion of toxic products. Diuretics, however, affect the electrolyte balance, increase blood viscosity and increase filtration load on insufficient nephrons. Moreover, systematic treatment with diuretics can result in other problems such as an overloading of the liver and other organs.

Preparations from natural sources have been used to stimulate the function of the nephrons. For example, lespecapitosides (lespenephril, Natermann, Spain) is used to treat uremia. This product has an uncertain effect on the kidney and often has cardiac and circulatory side effects. Moreover, this product does not provide the necessary regenerative building blocks and energy source to positively effect the kidney. Canrenoate potassium (Kanrenol, Boots, Italy) is also used to treat hyperaldosteronism and is used in patients with chronic renal insufficiency. Kanrenol suffers from many of the same draw backs as lespenephril.

Finally, diet foods, with undefined or crude protein constituants, have been used. The crude proteins are often insoluble in water and difficult to accurately incorporate into oral formulas. Moreover, there is uncertain utilization of the amino acids in such proteins by a patient suffering from chronic renal insufficiency. The undefined protein constituents are not readily utilizable and not sufficiently effective due to their poor digestion. The crude proteins contain salts and heavy metals.

As stated above, inappropriate or excessive administration of protein can result in hyperazotemia. Many prior art nutritional preparations, both oral or intravenous are comprised of both essential and non-essential amino acids. The use of currently available amino acids products can result in azotemia. Furthermore, some products are not appropriate for use by patients with chronic renal insufficiency due to the presence of hazardous levels of salts such as sodium chloride, sodium and potassium phosphates, and sulfates. For example, an oral protein hydrolysate briefly available, was Algomed (Nectacorp, Bulgaria). Algomed was an experimental product that proved unsatisfactory because of the high salt content, particularly high sodium phosphate level. Stark protein (Cernelle, Switzerland) is an oral protein supplement used by athletes.

Furthermore, oral or food products used in patients with chronic renal insufficiency use protein sources which are not sufficiently water soluble and thereby difficult to prepare a proper dose for a critically ill patients who can be maintained on oral therapy.

SUMMARY OF THE INVENTION

It is therefore, an object of the present invention to provide an oral preparation to be used by persons with metabolic disorders containing a natural energy source as well as a basic amino acid source rich in essential amino acids.

Another object of the present invention is to develop a method for preparation of protein hydrolysate, rich in essential amino acids and free of undesired salts, for use as an active ingredient in the oral preparation.

It is another object of the present invention to provide an oral preparation for use in patients with renal disease having a natural amino acid and caloric source that provides an appropriate carbohydrate to amino acid ratio.

It is yet another object of the present invention to provide an oral preparation that will stimulate synthesis of amino acids and proteins in the patient with chronic renal failure so as utilize some of the circulating nitrogen to reduce circulating nitrogen and improve metabolic processes.

It is still another object of the present invention to provide an oral preparation for use in patients with chronic renal insufficiency or other kidney or metabolic diseases that has a protein substrate that is water soluble to allow accurate dosing in critical patients.

Still another object of the present invention is to provide an oral preparation for use by patients with kidney disease or other metabolic disorders that has a balanced amino acid composition and, is free of undesired salts and heavy metals.

It is a further object of the present invention to provide an oral preparation for use by patient with chronic renal insufficiency that provides the patient with balanced amino acids and a readily utilizable energy source while eliminating undesired salts, limiting undesired amino acids, and low quality protein hydrolysates.

Still another object of the present invention is to provide an oral preparation for the treatment of patients with chronic renal insufficiency that will stimulate the reduction of circulating nitrogen in patients with chronic renal insufficiency by using a protein source rich in essential amino acids that are not deaminated, obtained from a natural source, are inexpensive to produce, and easy to combine with a readily utilizable, high caloric energy source.

Another object of the present invention is to provide an oral preparation for the treatment of patient with chronic renal insufficiency that utilizes a water soluble protein from a natural source, such as algae, blue-green algae, or fish combined, in an optimum ratio, with a naturally occuring high energy source, such as natural bee honey, to provide an oral preparation for use by patients with chronic renal insufficiency.

In accordance with the invention, briefly stated, an oral preparation for use in patients with chronic renal insufficiency or other metabolic disorders, and a method for the preparation of the protein hydrolysates, free of undesired salts used as an active principal in the oral preparation are provided, the oral preparation having a water soluble protein hydrolysate rich in essential amino acids derived from a natural source such as algae, blue-green algae or fish. The water soluble protein hydrolysate is combined with natural bee honey caloric source. Approximately five to thirty percent of the protein hydrolysate is combined with seventy to ninety-five percent natural bee honey. To provide an optimum calorie to protein ratio. The oral preparation is administered to a patient in a dose of thirty (30) to one hundred and fifty (150) grams per day divided into one to four daily meals. The preparation maybe administered orally or through a nasogastric feeding tube via a feeding pump.

DESCRIPTION OF THE PREFERRED EMBODIMENT

Figure 1:
FIG. 1 is an electron photomicrograph, enlarged 10×10. XE., of kidney tissue of an animal (rat) with chronic renal insufficiency induced by potassium chromate.

The oral preparation for use by patients with chronic renal insufficiency of the present invention is best illustrated by the examples contained hereinafter.

The preparation for the treatment of patients with chronic renal insufficiency has the following general formula:
ultrafiltered salt-free protein hydrolysate rich in essential amino acids from a natural source 5.0–30.0, preferably 15 grams; and natural bee honey 70.0 grams–95.0 grams, preferably 85 grams.

The preparation is administered to the patient, by mouth, in doses of thirty (30) to one hundred and fifty (150) grams per day in one to four doses per day. The dose is dependent upon the patient's calcium and protein requirements, response to thereby, and laboratory values.

To make the oral preparation of the present invention, dry water soluble protein hydrolysate is dissolved in hot water at a temperature up to 70° C. on a water bath at 80–90° C. A homogenizer, equipped with a mantle with circulating water, is used for this purpose. After homogenization is completed, the mixture is cooled down to 50° C. by running cold water through the mantle. At this temperature, the honey, which is prewarmed to 35°–40° C. honey is added with stirring. Stirring is continued for additional 30 minutes with a switch of the direction of the stirring at 15 minute intervals. When the temperature reaches 28°–30° C., the product can be packaged in glass jars, plastic packages or other appropriate containers.

The above stated protein hydrolysate is prepared from a natural source in accordance with the principles described in the Bulgarian Reference No. 60136, published Dec. 27, 1993 in the Bulletin Of The Patent Bureau, Bulgaria. The protein hydrolysate is prepared in a manner that reduces the contents of salts, toxic heavy metal, such as lead, arsenic, mercury, cadmium, maganese, nickel, copper and other heavy metals that are often included in food products. The preparation of the above stated protein hydrolysate is accomplished by the addition of water to a biomass of a naturally occuring protein source, such as green algae, blue-green algae (cyanobacteria), fish, or suitable vegetable protein such as soy protein. A biomass of aqua-cultered algae is particularly appropriate. Next, 0.05 to 0.1% calcium hydroxide and 0.2 to 2.0% alkaline protease (Subtilisin DY, 10,000 to 50,000 units per milliliter, Plastchism Company, Botevgrad City, Bulgaria) is added. Hydrolysis is then carried out at a temperature 35 to 70° C. for 90 minutes. The resulting mixture is filtered for the removal of solid particles and the filtrate is subjected to ultrafiltration through semipermeable membrane with pores of 3,000 to 300,000 Daltons.

More specifically, the protein hydrolysate used in the present invention can be prepared from the fish, Macroronus. To prepare the protein hydrolysate from the fish, Macroronus, a biomass of 1000 kg of fish Macroronus are added to 100 liters of water. Five hundred grams of calcium hydroxide, 1.6 liter purified alkaline protease (Subtilsin DY with activity of 50,000 units per ml), are added. The mixture is stirred with a mechanical stirrer at 55° C. for 90 minutes. The bones are separated by filtration and the filtrate, after centrifigation, is subjected to ultrafiltration through a semipermeable membrane. The ultrafiltrate is spray dryed to give 90 kilograms of dry protein hydrolysate as a white to pale beige powder with a weak fishy smell. The powder is water soluble and considerably hydroscopic under prolonged exposure to air.

Another, similar protein hydrolysate used in the present invention can also be prepared from microalgae as follows:

To 100 kilograms of dry green microalgae, species Scenedesmus, is added 800 liters of water, 500 grams of calcium hydroxide, and 400 ml of purified alkaline protease (Subtilisin DY with activity of 50,00 units per ml). The mixture is stirred with mechanical stirrer at 55° C. for 90 minutes. The obtained protein hydrolysate, after centrifigation, is subjected to ultrafiltration through a hydrophilic, semipermeable membrane. The ultrafiltrate is spray dried to produce 25 kg of dry protein hydrolysate having a white to pale beige color with a week specific odor. The powder is water soluble and hydroscopic under prolonged exposure to air.

The content of the toxic elements in the above prepared protein product, as compared to standards as provided by the Collective Official Documents On The Health Organization in Bulgaria, Vol. IX, pp. 166, 1987 are as follows:

| Parameter | According to the invention mg/kg | According to maximum allowable limits mg/kg |
| --- | --- | --- |
| lead | 0.19 | 1 |
| arsenium | ND* | 0.4 |
| copper | 0.45 | 3 |
| chromium | ND* | 0.5 |
| mercury | ND* | 0.04 |
| manganese | 0.17 | 1 |
| nickel | ND* | 0.4 |
| cadmium | 0.05 | 0.4 |
| zinc | 1.1 | 40 |
| nitrates | 7 | 300 |

* None Detected

A preferred source of the protein hydrolysate, heretofore undisclosed, is *Spirulina pacifica*, a blue-green algae (cyanobacteria). The novel method of preparation of protein hydrolysate from *Spirulina pacifica* will now be described.

The preparation of protein hydrolysates according to the Bulgarian patent #60136 (reg#91995) uses calcium hydroxide ($Ca(OH)_2$) to maintain the proper pH for the alkaline protease, thus introducing calcium to the biomass subject to hydrolysis. Although the concentration of calcium can be controlled by its additional precipitation as an insoluble salt, the ideal hydrolysis would be one that introduces no additional chemicals during the hydrolysis. An additional problem with the prior method is the formation of finely suspended particles, consisting of debri, lipids and nucleic acids from the hydrolysed algae, stabilized by accompanying surfactants, that persistantly remain suspended. This suspension fails to clarify upon centrifugation and clear solutions can be obtained only after ultrafiltration. The suspended matter gives high dead volumes of thick, viscous retentate that reduce the ultrafiltration flow rate by decreasing the membranes active surface.

The objective of this novel method for preparation of protein hydrolysates to be used in the oral preparation of the present invention addresses the above two problems. The objective is achieved by utilizing neutral protease (SOLVEY Enzymes Inc. Elkhart, Ind.). The hydrolysis is carried out at neutral pH (approx. 7.0) and with an enzyme concentration less than 1. There is no addition of calcium hydroxide. This manner of hydrolysis, followed by treatment with cellulase enzyme in a concentration less than 0.1%, gives clear solutions after centrifugation that can be directly spray-dried, thus avoiding the ultrafiltration step. This is not possible to achieve with the prior art method using the alkaline protease alone. The profound destructive effect of the cellulose on the suspension is due to hydrolysis of surfactants that contain hydrophilic sugar moieties, i.e. glycolipids, that get cleaved, resulting in collapse of the fine, stable suspension. Microscopically, the formation of oily droplets, brightly colored in yellow by the disolved carotene, is observed. The finely suspended particles readily aggregate and are easily separated by simple centrifugation alone.

The following is an example of the novel method of preparing protein Hydrolysate from *Spirulina pacifica*.

Approximately 900 liters of water is added to approximately 100 kg of spray-dried *Spirulina pacifica* (Cyanotech Corporation, Hawaii), to make a mixture of the Spirulina in water. The mixture is mechanically stirred and heated to 55° C. Approximately 100 g. of neutral protease (Optimase APL-440FG, having an activity of 440 DAPU/g obtained from *Bacillus licheniformis*, Solvey Enzymes, Inc., Ekhart, Ind.) is added to the mixture. Hydrolysis is continued for approximately two (2) hours resulting in a hydrolysate solution. The hydrolysate solution is treated with cellulase (activity of 100,000 ECU/g, ALKO Ltd. Biotechnology, Rajamaki, Finland), with simultaneous centrifugation, closed cycle for approximately 30 minutes until clarification is achieved. The clear solution is ultrafiltered and the ultrafiltrate is spray-dried resulting in approximately 80 kg of protein hydrolysate.

An additional advantage of the above methods for the preparation of the protein hydrolysates for use in the novel oral preparation is the removal of non-protein nitrogen from purine nucleosides in the form of nucleic acids. In man, uric acid is the major product of the catabolism of the purine nucleosides, adenosine and guanosine, under the activity of adenosine deaminase and guanase. This catabolism is accompanied by the simultaneous liberation of ammonia and its conversion into urea. Dietary sources contribute about 40% of the uric acid found in man. However, about 60% is obtained by degradation of endogenous nucleic acids. On the other hand the de novo synthesis of nuclesides in the presence of a purine depleated diet utilizes endogenous ammonia.

It will be apparent that the protein hydrolysate may be obtained from any appropriate natural source, either marine, aqua-cultured, or terrestial that provide the optimal protein content, without departing from the scope of the appended claims. Furthermore, any appropriate high density calorie source may be used. Therefore, the foregoing examples should be viewed as illustrative only.

EXAMPLES OF THE USE OF THE NOVEL ORAL PREPARATION

Example 1
Effect On An Experimental Model Of Nephropathy In Rats.

Experiments were carried out with mature male rats weighing 180–200 g. The animals were divided in the following groups of 15: control group, control group treated with potassium chromate (17.5 mg/kg applied under the skin) to create nephropathy, and three experimental groups treated with natural honey, fish protein hydrolysate and the oral preparation (protein hydrolysate+honey) in a dose of 500 mg/kg per os, respectively. The treatment with tested components was initiated 3 days before and 18 days after the application of potassium chromate. A comparative study of the following parameters was performed:

1. urine (protein, sediment, 24 hours volume)—before and at the end of the experiment;
2. The animals were sacrificed at the end of the experiment and their blood was collected in dry test tubes, centrifuged at 2000 rpm and the plasma separated for the determination of the following parameters:
   a. Microelements: sodium, potassium, calcium, chlorides and phosphorous;
   b. Lipid parameters: cholesterol, triglycerides, HDL, LDL, VLDL, VHDL cholesterol;
   c. Enzyme activity of: lactodehydrogenaze (LDH), creatinephosphokinase (CPK), aspartateaminotransferase (ASAT) and alaninaminotransferase; d. Other biochemical parameters: urea, creatinine and uric acid.
3. After collection of the blood, the kidneys and the liver were taken for microscopic studies. For the purpose these organs were fixed in 10% formol-calcium, sliced by microtome and colored (dyed) with hematoxylin-eosin.

The results from the experiments showed that the control group treated with potassium chromate (FIG. 1) developed a typical intoxication pattern within 2–3 days, the animals gradually lose weight, their urine has very high levels of protein and about 20% die by the end of the experiment. The analysis of their serum showed higher levels of phosphorous, and to a smaller extent of the chlorides, compared to that of untreated controls. The levels of creatinine, urea and uric acid are significantly increased. To a smaller degree, cholesterol and triglyceride level are increased, while the values for HDL are lower compared to the untreated. The enzyme activity of the transaminases and LDH is reduced. The microscopic observations showed that the controls treated with potassium chromate developed very severe forms of damage of the kidney structure, as shown in FIG. 1. Multiple blood lesions, numerous holes in the tubules and fibroblasts were also observed in kidney tissue from individual animals.

Figure 2:
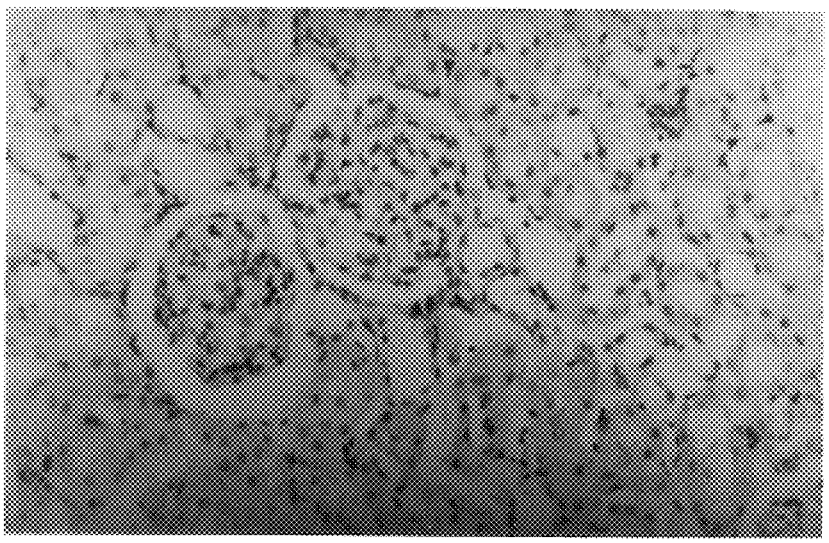
FIG. 2 is an electron photomicrograph, enlarged 10×10. XE., of the kidney tissue of a control animal (rat)
Figure 3:
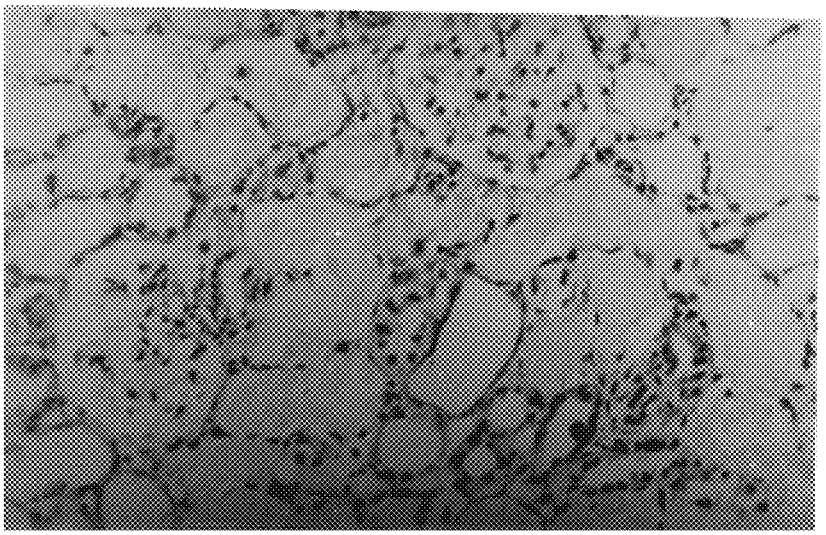
FIG. 3 is an electron photomicrograph, enlarged 10×10. XE., of kidney tissue of an animal (rat) with chronic kidney insufficiency induced by potassium chromate after four (4) days of treatment with the protein hydrolysate component of the oral preparation of the present invention.
Figure 4:
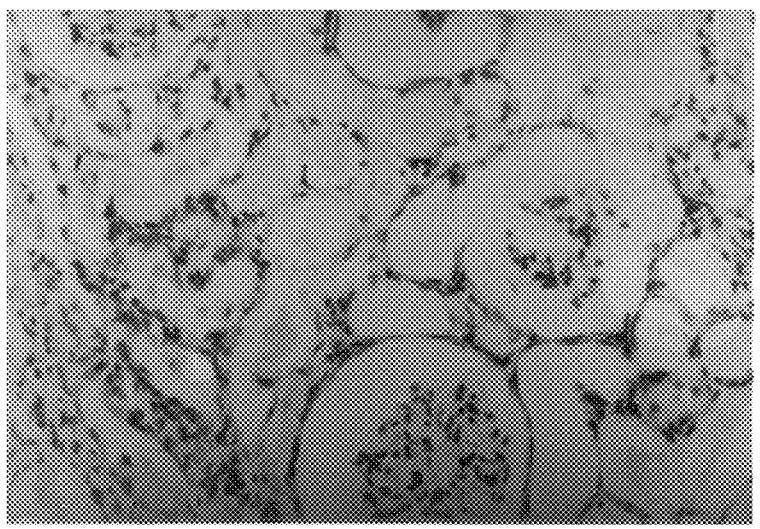
FIG. 4 is an electron photomicrograph, enlarged 10×10. XE., of kidney tissue of an animal (rat) showing with chronic renal kidney insufficiency induced by potassium chromate after eighteen (18) days of treatment with protein hydrolysate component of the healing food of the present invention.

The survival is greater (up to 100%) in the control groups, with the microscopic evaluation of the kidney tissue as shown in FIG. 2, and, in particular, the group treated with the oral preparation of the present invention, the microscopic tissue evaluation shown in FIGS. 3 and 4.

The general condition is less affected in the case of the group treated with honey alone. The levels of phosphorous are lowest in the case of the treatment with the combination preparation. The microelements are not significantly changed compared to the controls. While the bee honey has a negligible effect on the concentration of urea, creatinine and uric acid, which are increased by the action of the chromate, the hydrolysate alone and the oral preparation in particular lower considerably the values of these parameters, as shown in the following Table 1:

TABLE 1

COMPERATIVE STUDIES ON THE EFFECT OF ORAL PREPARATION ON SOME CLINICAL PARAMETERS OF SERUM IN ROMA RAT WITH INDUCED NEPHROPATIA, AFTER 18 DAYS OF TREATMENT

| Parameters | Controls untreated | Controls treated K2CrO7 | Treated with K2CrO7 and ingr. A* | K2CrO7 treated and Ingr. B* | K2CrO7 treated and ingr. A + B* |
|---|---|---|---|---|---|
| Potassium | 5.9 ± 0.76 | 7.40 ± 0.66 | 7.2 ± 1.14 | 5.9 ± 0.9 | 5.4 ± 0.43 |
| Soldium | 145 ± 12.0 | 152.4 ± 3.6 | 149.7 ± 0.66 | 148.2 ± 4.6 | 147.7 ± 5.6 |
| Chlorides | 108.8 ± 2.9 | 118.7 ± 2.6 | 112.0 ± 2.7 | 109.2 ± 3.8 | 107.6 ± 2.4 |
| Calcium | 3.7 ± 0.76 | 3.4 ± 0.66 | 3.68 ± 0.7 | 2.47 ± 0.5 | 3.2 ± 0.14 |
| Phosphorous | 2.2 ± 0.2 | 2.94 ± 0.32 | 2.89 ± 0.39 | 2.39 ± 0.31 | 2.24 ± 0.2 |
| Urea | 11.2 ± 1.8 | 13.58 ± 2.6 | 13.2 ± 2.6 | 12.1 ± 2.2 | 11.8 ± 1.9 |
| Creatinine | 89.6 ± 11.9 | 98.8 ± 16.7 | 96.2 ± 20.1 | 91.6 ± 23.4 | 90.9 ± 18.5 |
| Uric acid | 332.1 ± 98 | 383.8 ± 79 | 388.6 ± 101 | 354.0 ± 107 | 342.2 ± 94 |
| Cholesterol | 2.27 ± 0.5 | 2.59 ± 0.7 | 2.48 ± 0.6 | 2.14 ± 0.6 | 2.30 ± 0.5 |
| Triglycerides | 1.78 ± 0.3 | 1.93 ± 0.4 | 1.98 ± 0.4 | 1.64 ± 0.4 | 1.60 ± 0.5 |
| HDL | 1.25 ± 0.2 | 1.09 ± 0.26 | 1.15 ± 0.34 | 1.12 ± 41 | 1.30 ± 0.3 |
| LDL | 0.67 | 0.76 | 0.72 | 0.70 | 0.68 |
| VDDL | 0.41 | 0.46 | 0.43 | 0.33 | 0.39 |
| ASAT | 114 | 82 | 108 | 99.0 | 112 |
| ALAT | 82 | 49 | 59 | 669 | 73 |
| CPK | 1029 | 708 | 816 | 900 | 985 |
| LDH | 1503 | 1673 | 1668 | 1587 | 1532 |
| GGT | 11 | 5 | 5 | 5 | 7 | a) Statistical factor for above values P 0.5,
b) Aspartate aminotransferase (ASAT),
c) Alanine aminotransferase,
d) Creatinine phosphokinase (CPK),
e) Lactate dehydrogenase (LDH)
*Ingredient A = method bee honey: Ingredient B = protein hydrolysate: Ingredient A + B = oral preparation of the present invention.

(Table 1). The lipid parameters are not changed significantly under the action of the chromate but still a small tendency can be seen for an increase of the major atherogenic lipids: cholesterol, triglycerides and LDL. From this standpoint the protein hydrolysate alone and the oral preparation decrease to an equal degree the values for the above parameters. The oral preparation has the most pronounced prophylactic and healing effect on the disorders of enzymatic activity individual by the potassium chromate. The histological preservation of the structure is observed mainly in the group treated with the oral preparation are shown in FIGS. 3 & 4.

Example 2

Effect On A Model Of Liver Damage Of Rats With Tetrachloromethane (carbon tetrachloride).

The experiments were performed with 40 male rats strain VISTAR, divided in the following groups of 10: control treated with 0.5 mL/100 g tetrechloromethane and three experimental treated in advance (3 days) with the tested formulation. The treatment was continued to the end of the experiment—till the 7th day after the tetrachloromethane. The effect of the natural honey, the protein hydrolysate and the combination i.e. the oral preparation of the present invention, healing food (500 mg/kg per os) were also studied on model liver lesions induced by tetrachloromethane.

The results of the experiments showed that the control group develops necrotic processes in the liver. Multiple blood lesions and leucocytic infiltration were histologically observed around the major blood vein. A defined fatty dystrophy is observed. The pathological changes in the groups treated with the fish hydrolysate alone and the oral preparation (i.e. hydrolysate & honey) were much less pronounced: the leucocytic infiltration is observed only in separate zones, the liver shows with preserved structure, and no changes of the circulartory system. No significant histological difference was observed in the case of preparations of animals treated with the fish hydrolysate alone or with the oral preparation, Example 3

Comparative Study Of The Effect On Model Hyperlipoproteinemia Of Rats.

The experiments were carried out with 100 male rats, divided in 5 groups, 20 each: controls untreated, controls—on a cholesterol diet and three experiments treated with protein hydrolysate alone, the oral preparation, in 500 mg/kg doses per os' and phenophybrate in 100 mg/kg doses per os respectively. After three weeks the animals were sacrificed, their blood collected and, after centrifigation the plasma lipids and enzymes were analyzed. Parenchymations organs were also collected for histological analysis.

The results of the studies showed that the levels of the major atherogenic factors i.e.cholesterol, VLDL, LDL and the triglycerides are increase under the conditions of a cholesterol diet. The serum cholesterol level in the groups treated with fish hydrolysate alone and oral preparation are considerably reduced in comparison with the group on cholesterol diet, and remain below the levels of the untreated controls. In the same manner the levels of LDL and VLDL decreased, while HDL increased. Phenophybrate, used as a reference for comparison, has similar effect but does not significantly change the parameters, as illustrated by Table 2:

TABLE 2

EFFECT OF HYPERLIPOPROTENINEMIA IN RAT

| Parameters | Controls untreated | Controls cholesteral | Cholesterol honey diet | Cholesterol + hydrolysate | K2CrO7 & oral preparation |
|---|---|---|---|---|---|
| 1. Cholesterol | 2.2 ± 0.25 | 3.17 ± 0.59 | 3.02 ± 0.45 | 2.75 ± 0.54 | 2.34 ± 0.45 |
| 2. HDL | 1.31 ± 0.41 | 1.19 ± 0.40 | 1.22 ± 0.38 | 1.57 ± 0.25 | 1.37 ± 0.16 |
| 3. LDL | 0.46 ± 0.18 | 1.58 ± 0.51 | 1.36 ± 0.60 | 0.69 ± 0.64 | 0.53 ± 0.45 |
| 4. VLDL | 0.95 ± 0.34 | 1.29 ± 0.23 | 1.07 ± 0.34 | 0.61 ± 0.11 | 0.56 ± 0.25 |
| 5. Triglycerides | 2.29 ± 0.55 | 2.88 ± 0.43 | 2.74 ± 0.85 | 2.28 ± 0.23 | 1.96 ± 0.75 |
| 6. ASAT | 131 ± 33 | 136 ± 23 | 135 ± 34 | 138 ± 32 | 136 ± 21 |
| 7. ALAT | 86 ± 25 | 80 ± 15 | 88 ± 38 | 85 ± 11 | 87 ± 16 |
| 8. HBDH | 617 ± 153 | 551 ± 144 | 568 ± 1124 | 557 ± 117 | 588 ± 134 |
| 9. CPK | 1128 ± 224 | 845 ± 167 | 985 ± | 1086 ± 201 | 1110 ± 165 | x - Statistical factor in relation to group 1
*Statistical factor in relation to group 11

Figure 5:
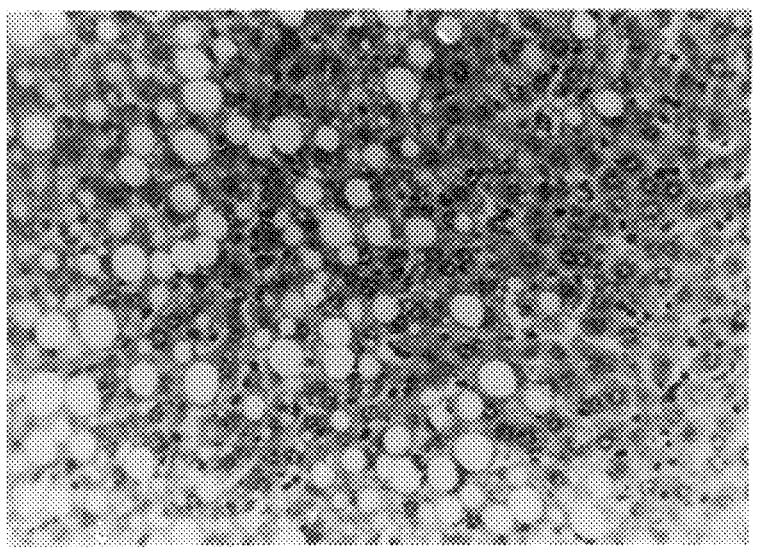
FIG. 5 is an electron photomicrograph, enlarged 10×10, of kidney tissue of an animal (rat) with high cholesterol diet, used as a controlled.

All studied preparations did not affect the HBDH and ASAT activity, which are slightly changed under the influence of the cholesterol diet. Phenophybrate shows similar effect. The histological examination showed that the cholesterol diet causes the most changes in the liver, where a complete or a partial lipid infiltration is observed in FIG. 5.

Figure 6:
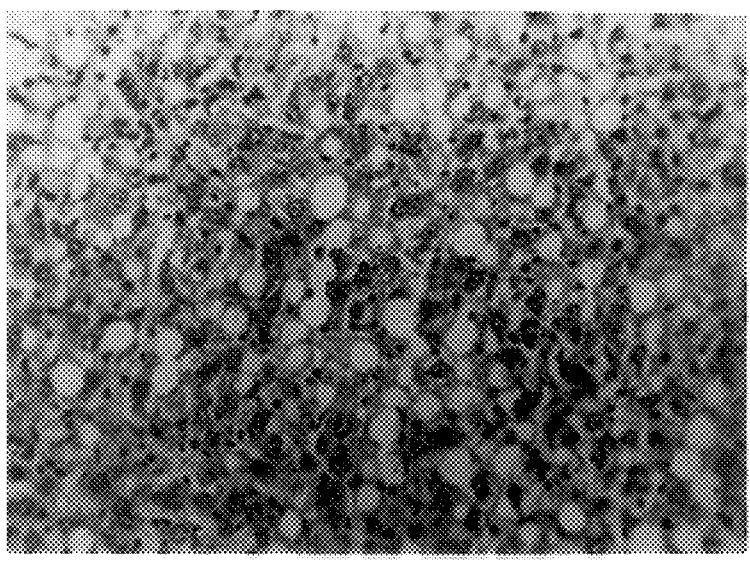
FIG. 6 is an electron photo micrograph, enlarged 10×10, of kidney tissue of an animal (rat) on a cholesterol diet treated with the oral preparation of the present invention, showing a reduction of lipid infiltration.

The lipid infiltration is less pronounced in the cases of treatment with hydrolysate alone, the oral preparation, or phenophybrate. See FIG. 6. Small fatty vaccuoles or individual lipid inclusions were observed. Phenophybrate has a more pronounced effect.

Example 4

Effect On The Static Physical Tolerance After One Month Treatment In Rats.

The experiments were carried out with 40 male rats divided into 4 equal groups: control untreated, treated with honey, treated with hydrolysate alone and the formulated oral preparation (hydrolysate+honey) over the course of one month. Before the treatment, and on every 5th day to the end of the treatment, the animals were placed in the compartment for study of the static physical tolerance. Simultaneously with the tolerance measurements, the tolerance to electric current impact as test for stress damage was measured.

The results of the experiments are summarized in Table 3:

TABLE 3

EFFECT OF STATIC PHYSICAL TOLERANCE AND RESISTANCE AGAINST ELECTRIC CURRENT AFTER 30 DAYS TREATMENT

| Groups of rats | Physical tolerance before treatment | treatment | % | Resistance to electricity before treatment | after treatment | % |
|---|---|---|---|---|---|---|
| 1. Controls | 462 ± 48 | 698 ± 78 | 51 | 506 ± 66 | 720 ± 89 | 42 |
| 2. Bee honey | 512 ± 52 | 738 ± 76 | 54 | 746 ± 92 | 906 ± 102 | 22 |
| 3. Fish hydrolystate | 499 ± 96 | 864 ± 106 | 73 | 728 ± 90 | 1285 ± 186 | 79 |
| 4. Healing food | 480 ± 55 | 870 ± 96 | 81 | 638 ± 74 | 1223 ± 101 | 92 | x - Statistical factor (P 0.05)

As it can be seen from the table, only the group treated with the oral preparation demonstrates a considerable static physical tolerance. The stability to electric current impact increases in the group treated with hydrolysate alone, but the effect is greater in the group treated with oral preparation.

Example 5
Toxicological Studies.

Feeding the oral preparation of the present invention by mouth in doses up to 5.0 g/kg body weight did not cause toxic changes or death. The oral preparation is practically non-toxic. Testing over six months to determine chronic toxicity in white rats of doses of 2.0 and 5.0 g/kg body weight did not lead to toxicologic changes in the tested clinical-laboratory and morphological parameters.

Example 6
Clinical Study Of The Oral Preparation.

The study was performed with 32 patients with different degree of chronic renalinsufficiency (CRI) with serum creatinine values ranging from 201 to 1193 umoL/L (the norm being up to 134 umoL/L. The treated patients presented with the following major diagnoses: Balkan endemic nephropathy—4; lupus nephropathy—1; chronic glomerulonephritis—5; podagric nephropathy—4; kidney (renal) polycystosis—5; chronic pyelonephritis—13.

Upon a background of a low protein diet with daily protein intake of 0.6 to 0.40 g/kg/24 h, depending upon the degree of the kidney insufficiency, 100 g of the oral preparation made in accordance with the principles of the present invention, was given daily to the patients in the divided doses. The course of treatment was 120 days. The paraclinical parameters, characterizing the hemopoiesis, protein and lipid metabolism, electrolyte balance, as well as the urine excretion of urea, creatinine and electrolytes were monitored from the beginning and every 30 days to the end of the treatment in order to evaluate the therapeutic effect.

The results from the clinical studies at the end of the treatment demonstrated that the hemopoiesis was favorably affected.

The changes in the values of the parameters related to the protein metabolism are presented below in Table #4.

TABLE 4

| | before the treatment | after the treatment | P |
|---|---|---|---|
| EFFECT OF HOMOPOIESIS | | | |
| hemoglobin g/L | 98 ± 17 | 110 ± 19 | p 0.05 |
| erythrocytes B/L | 3.16 ± 0.5 | 3.8 ± 0.9 | p 0.05 |
| leucoytes g/L | 6340 ± 1130 | 6765 ± 970 | p 0.05 |
| rpe mm/h | 72/95 ± 15/28 | 28/48 ± 8/22 | p 0.05 |
| CHANGES IN THE PROTEIN METABOLISM | | | |
| total blood protein | 66 ± 7 | 70 ± 5 | — |
| albumins g/L | 33 ± 3.6 | 38 ± 4.2 | p__0.05 |
| blood urea moL/L | 18 ± 6 | 10 ± 3 | p__0.01 |
| creatinine moL/L | 384 ± 112 | 228 ± 98 | p__0.01 |
| uric acid moL/L | 434 ± 48 | 365 ± 32 | p__0.01 |
| creative clearance nmol/240 | 19.2 ± 5.2 | 19.4 ± 6.9 | p 0.01 |
| CHANGES IN THE BLOOD SUGAR AND TRANSAMINASES | | | |
| blood sugar MmoL/L | 5.2 ± 1.03 | 4.8 ± 0.9 | |
| ASAT U/L | 10.3 ± 3.2 | 12.2 ± 5.1 | |
| ALAT U/L | 8.6 ± 5.8 | 9.6 ± 6.2 | |
| CHANGES IN THE SERUM ELECTRONICS | | | |
| sodium mmoL/L | 145 ± 4.7 | 143.6 ± 2.9 | p 0.05 |
| potasium mmoL/L | 5.15 ± 0.53 | 4.64 ± 0.65 | p 0.05 |
| chloride mmoL/L | 110.8 ± 3.32 | 109.4 ± 3.56 | p 0.05 |
| calcium mmoL/L | 2.67 ± 0.33 | 2.61 ± 0.24 | p 0.05 |
| phosphorous MmoL/L | 1.41 ± 0.24 | 1.39 ± 0.25 | p 0.05 |
| CHANGES IN THE URINE EXCRETION | | | |
| urea mmoL/24 h | 275 ± 113.7 | 235 ± 106.7 | |
| creatinine MmoL/24 | 12345 ± 29.46 | 113.94 ± 32.21 | |
| calcium mmoL/24 h | 1.04 ± 0.7 | 1.4 ± 0.58 | p__0.05 |
| phosphorous Mmol/24 h | 6.67 ± 2.3 | 6.51 ± 2.8 | |

The average levels of the levels of the total blood protein and the albumins before and after the treatment remained in the normal range. Four of the patients with lupus nephrotic syndrome were with a defined hypoproteinemia (average levels of blood protein—5.2 g/L) and hypoalbuminemia (average levels of albumins—2.6 g/L). At the end of the treatment their treatment the levels were normalized demonstrating that the oral preparation can be used for treatment of the protein deficit in nephrotic syndrome.

The most important effect is the reduction of the levels of blood urea, serum creatinine and uric acid. There was a statistically significant increase in the hemoglobin level as well as the number of erythrocytes and their rate of precipitation. The number of leucocytes remained unaffected during the course of treatment. Of great importance is the significant decrease of the blood urea and the serum creatinine. At the same time there was no increase of their urea excretion, which suggests the increased reutilization of the non-protein nitrogen from the urea and creatinine. The levels of the total blood protein and the albumins in the patients with lupus nephrotic syndrome, were normalized demonstrating that the oral preparation can be used for treatment of the protein deficit in nephrotic syndrome.

The initial values of the parameters, characterizing the carbohydrate and lipid turnover as well as the electrolyte balance, remained unchanged to the end of the course of treatment.

Side effects or intolerance were not observed during the course of the treatment.

The oral preparation of the present invention favorably affects the key paraclinical and clinical symptoms of chronic renal insufficiency (CRI)—i.e. azotemia and anemia. The preparation finds wide application in the conservative treatment of patients with CRI and can contribute to a considerable extension of the pre-dialysis period of such patients thereby postponing costly and unpleasant hemodialysis treatment.

The healing effect of the aforedescribed oral preparation is a function of the additive effect of the metabolic substrates as provided by the novel protein hydrolysate and the high-energy containing of the natural bee honey. The afore described ratio of the two components provides for protein synthesis in the patient even during the condition of azotemia and intoxication caused by nitrogen retention. The optimal calorie to protein ratio of the oral preparation enhances the natural utilization of the undesired circulating nitrogen.

The foregoing description and examples are intended to be illustrative only. For example, the appended claims are intended to cover protein hydrolysates derived from any analgous natural sources, both marine and terrestrial, such as other appropriate green algae, aqua-cultered green algae, blue-green algae (cyanobacteria) or fish. Furthermore, it will be apparent that the scope of the invention covers variable ratios of calories to protein.

We claim:

1. A method of making an oral preparation comprising approximately 15% by weight of enzymatically derived protein hydrolysate and approximately 85% by weight bee honey for the treatment of elevated blood urea, serum creatinine, and uric acid in a patient with renal insufficiency, comprising:

dissolving dry, water soluble ultrafiltered, salt-free enzymatically derived protein hydrolysate in hot water having a temperature of up to 70° C. to form a protein hydrolysate in water mixture;

homogenizing the protein hydrolysate in water mixture;

cooling the homogenized mixture to 50° C.;

prewarming bee honey to approximately 35° C. to approximately 40° C.; and adding the prewarmed honey to the homogenized mixture to form a composition comprising approximately 15% by weight of enzymatically derived protein hydrolysate and approximately 85% by weight bee honey.

2. The method of claim 1 wherein the enzymatically derived protein hydrolysate is derived from the blue-green algae, *Spirulina pacifica*.

3. A method or reducing the levels of blood urea, serum creatinine, and uric acid in a patient with renal insufficiency comprising:

feeding the patient an oral preparation consisting essentially of approximately 5% to approximately 30% ultrafiltered enzymatically derived protein hydrolysate enzymatically derived from a protein source and honey.

4. The method of claim 3 further comprising feeding the patient approximately 30 grams to approximately 150 grams of the oral preparation per day in one or more feedings.

5. The method of claim 3 wherein the oral preparation comprises approximately 70% to approximately 95% bee honey, by weight.

6. The method of claim 3 wherein the protein source is selected from the group comprising the fish, Macroronus and the blue green algae *Spirulina pacifica*.

7. An oral preparation for the treatment of elevated blood urea, serum creatinine, and uric acid in a patient with renal insufficiency patients or other metabolic disease, consisting essentially of:

approximately 5% to approximately 30% ultrafiltered, salt-free enzymatically derived protein hydrolysate derived from a protein source; and approximately 70% to approximately 95% bee honey.

8. The oral preparation of claim 7 wherein the protein source of the ultrafiltered, salt-free enzymatically derived protein hydrolysate is a marine source selected from the group consisting of the blue green algae *Spirulina pacifica* and the fish Macroronus.

9. The oral preparation of claim 7 wherein the protein source of the ultrafiltered, salt-free enzymatically derived Protein hydrolysate is a natural plant protein selected from the group consisting of soy protein, wheat protein and similar plant proteins having an amino acid content similar to soy protein and wheat protein.

* * * * *

UNITED STATES PATENT AND TRADEMARK OFFICE
CERTIFICATE OF CORRECTION

PATENT NO. : 5,935,605  
DATED : August 10, 1999  
INVENTOR(S) : Stoilov et al.

Page 1 of 1

It is certified that error appears in the above-identified patent and that said Letters Patent is hereby corrected as shown below:

Column 1,
Line 30, replace "psycological" with -- psychological --

Column 3,
Line 61, replace "maybe" with -- may be --

Column 11,
Line 2, replace "EFFECT OF" with -- EFFECT ON --
Line 5, insert -- After -- above the word "treatment"

Column 12,
Line 53, replace "the treatment their treatment" with -- their treatment --

Signed and Sealed this

Fourth Day of February, 2003

JAMES E. ROGAN
*Director of the United States Patent and Trademark Office*